United States Patent
Jäger et al.

(10) Patent No.: US 10,968,466 B2
(45) Date of Patent: Apr. 6, 2021

(54) PROCESS FOR PREPARING AMINOBENZOIC ACID OR AN AMINOBENZOIC ACID CONVERSION PRODUCT

(71) Applicant: COVESTRO DEUTSCHLAND AG, Leverkusen (DE)

(72) Inventors: Gernot Jäger, Cologne (DE); Ivonne Görtz, Cologne (DE); Giulio Lolli, Cologne (DE); Amgad Salah Moussa, Bad Säckingen (DE); Thomas Hamedinger, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 94 days.

(21) Appl. No.: 16/469,746

(22) PCT Filed: Dec. 18, 2017

(86) PCT No.: PCT/EP2017/083374
§ 371 (c)(1),
(2) Date: Jun. 14, 2019

(87) PCT Pub. No.: WO2018/114841
PCT Pub. Date: Jun. 28, 2018

(65) Prior Publication Data
US 2019/0382812 A1    Dec. 19, 2019

(30) Foreign Application Priority Data

Dec. 20, 2016 (EP) .................................... 16205348
Nov. 27, 2017 (EP) .................................... 17203706

(51) Int. Cl.
| | | |
|---|---|---|
| C12P 13/00 | (2006.01) | |
| C07C 209/78 | (2006.01) | |
| C07C 227/40 | (2006.01) | |
| C07C 231/02 | (2006.01) | |
| C07C 245/02 | (2006.01) | |
| C08G 12/08 | (2006.01) | |
| C08G 73/02 | (2006.01) | |

(52) U.S. Cl.
CPC .......... *C12P 13/005* (2013.01); *C07C 209/78* (2013.01); *C07C 227/40* (2013.01); *C07C 231/02* (2013.01); *C07C 245/02* (2013.01); *C08G 12/08* (2013.01); *C08G 73/026* (2013.01)

(58) Field of Classification Search
CPC .................................................. C07C 227/40
See application file for complete search history.

(56) References Cited

U.S. PATENT DOCUMENTS

| | | |
|---|---|---|
| 4,233,459 A | 11/1980 | Kilpper et al. |
| 4,328,339 A | 5/1982 | Kilpper et al. |
| 4,851,570 A | 7/1989 | Zaby et al. |
| 5,053,539 A | 10/1991 | Yano et al. |
| 5,286,760 A | 2/1994 | Bolton et al. |
| 6,433,219 B1 | 8/2002 | Strofer et al. |
| 2006/0025556 A1 | 2/2006 | Koch et al. |
| 2006/0287555 A1 | 12/2006 | Hagen et al. |
| 2007/0203364 A1 | 8/2007 | Dugal et al. |
| 2007/0238901 A1 | 10/2007 | Dugal et al. |
| 2007/0299279 A1 | 12/2007 | Pohl et al. |
| 2009/0065347 A1 | 3/2009 | Sommer et al. |
| 2009/0175121 A1 | 7/2009 | Rausch et al. |
| 2010/0324336 A1 | 12/2010 | Sommer et al. |
| 2014/0371418 A1 | 12/2014 | Ng et al. |
| 2017/0152535 A1 | 6/2017 | Jaeger et al. |
| 2018/0371512 A1 | 12/2018 | Jaeger et al. |

FOREIGN PATENT DOCUMENTS

| | | |
|---|---|---|
| CN | 1923799 A | 3/2007 |
| CN | 103408177 B | 11/2013 |
| GB | 1201472 A | 8/1970 |

OTHER PUBLICATIONS

International Search Report, PCT/EP2017/083374, dated Feb. 12, 2018; Megido, Benigno.
Cooney and Wijaya, Effect of pH and Added Salts on the Adsorption of Ionizable Organic Species onto Activated Carbon from Aqueous Solution, Proceedings of the Second Engineering Foundation Conference on Fundamentals of Adsorption, May 4-9, 1986, p. 185-194, California.
Wiklund et al., The Chemistry of Anthranilic Acid, Current Organic Synthesis, 2006, p. 379-402, vol. 3.
Balderas-Hemandez et al., Metabolic Engineering for Improving Anthranilate Synthesis from Glucose in *Escherichia coli*, Microb. Cell. Fact., 2009, p. 19, vol. 8.
Gupta, Bhavana et al., Synthesis of functionalized conducting polymer "polyanthranilic acid" using various oxidizing agents and formation of composites with PVC, Polymers Advanced Technologies, 2011, p. 1982-1988, vol. 22 (abstract).

*Primary Examiner* — Bin Shen
(74) *Attorney, Agent, or Firm* — Donald R. Palladino

(57) ABSTRACT

The present invention relates to a process for preparing aminobenzoic acid or an aminobenzoic acid conversion product, comprising the steps of: (I) providing an aqueous solution of aminobenzoic acid using a fermentation process; (II) adsorbing aminobenzoic acid; (III) desorbing aminobenzoic acid at a pH in the range from −0.8 to 3.0, preferably −0.5 to 3.0, more preferably 0.1 to 3.0, very preferably 0.5 to 2.5, very exceptionally preferably 1.0 to 2.0; (IV) obtaining the aminobenzoic acid from the desorbate obtained in step (III); (V) optionally further converting the aminobenzoic acid obtained in step (IV) to an aminobenzoic acid conversion product.

9 Claims, No Drawings

PROCESS FOR PREPARING AMINOBENZOIC ACID OR AN AMINOBENZOIC ACID CONVERSION PRODUCT

CROSS-REFERENCE TO RELATED APPLICATION

This application is a national stage application under 35 U.S.C. § 371 of PCT/EP2017/083374, filed Dec. 18, 2017, which claims the benefit of European Application No. 16205348.2, filed Dec. 20, 2016 and European Application No. 17203706.1, filed Nov. 27, 2017, each of which are incorporated by reference herein.

The present invention relates to a process for preparing aminobenzoic acid or an aminobenzoic acid conversion product, comprising the steps of:
  (I) providing an aqueous solution of aminobenzoic acid using a fermentation process;
  (II) adsorbing aminobenzoic acid;
  (III) desorbing aminobenzoic acid at a pH in the range from −0.8 to 3.0, preferably −0.5 to 3.0, particularly preferably 0.1 to 3.0, very preferably 0.5 to 2.5 and extremely very particularly preferably 1.0 to 2.0;
  (IV) obtaining the aminobenzoic acid from the desorbate obtained in step (III);
  (V) optionally further reacting the aminobenzoic acid obtained in step (IV) to give an aminobenzoic acid conversion product.

BACKGROUND

Aminobenzoic acid is an economically important product which is used either as such or as an intermediate in the preparation of other compounds derived from the aminobenzoic acid by further chemical reaction(s) (aminobenzoic acid conversion products, also referred to as aminobenzoic acid derivatives). For example, aminobenzoic acid is used in the preparation of dyes, odorants or pharmaceuticals (Wiklund, Current Organic Synthesis, 2006, 3, 379-402). An example of an important aminobenzoic acid conversion reaction for the preparation of another product is decarboxylation to give aniline, which is, on its part, of importance especially as an intermediate in the preparation of isocyanates.

Aminobenzoic acid can be obtained by chemical means or by fermentation:

The chemical preparation of aminobenzoic acid is described in the literature. A suitable synthesis route (with yields>98%) is, for example, the reaction of phthalimide with sodium hypochlorite.

Phthalimide can, on its part, be obtained from phthalic anhydride and ammonia. The whole process is well-known and is described, for example, in Lorz et al., *Phthalic Acid and Derivatives in Ullmann's Encyclopedia of Industrial Chemistry, Volume* 27, pp. 140-141, Weinheim, Wiley-VCH. An industrial process is also described in the patent literature; see e.g. DE 29 02 978 A1 and EP 0 004 635 A2.

CN 103408177 B deals with the treatment and recycling of wastewater from chemical anthranilic acid production. The chemical synthesis route described is the reaction of phthalic anhydride with urea in excess to form phthalimide, the decomposition thereof with sodium hypochlorite under alkaline conditions, followed by acidification of the sodium salt thus formed with hydrochloric acid. The anthranilic acid thus formed is removed by centrifugation and washed. The aqueous phase arising in the centrifugation and the wash water are aqueous wastewaters which mainly contain unreacted phthalimide, anthranilic acid and sodium chloride. The cleaning of such wastewaters is the subject matter of this patent specification.

Said cleaning comprises, in a step a), the adjustment of the pH of the wastewater to 8, followed by conduction of the thus alkalinized wastewater through an adsorption column filled with a chemically modified highly crosslinked polystyrene-divinylbenzene adsorption resin. The wastewater obtained in this cleaning step a) is then adjusted in a step b) with 1 to 2% hydrochloric acid to a pH of 5 and conducted through an adsorption column filled with a chemically modified highly crosslinked polystyrene-divinylbenzene adsorption resin.

When the adsorption column from step a) is almost saturated, it is replaced in a step c) with a parallely connected adsorption column of the same type, and the column taken out of operation is regenerated. For this purpose, the adsorption column is first flushed through with 4 to 6% hydrochloric acid and then with 1 to 2% sodium hydroxide solution. The wastewater arising in the course of this is combined with the original wastewater solution.

When the adsorption column from step b) is almost saturated, it is likewise replaced in a step d) with a parallely connected adsorption column of the same type, and the column taken out of operation is regenerated. For this purpose, the adsorption column is first flushed through with 4 to 6% sodium hydroxide solution and then with 1 to 2% hydrochloric acid. The wastewater arising in the course of this is combined with the original wastewater solution.

CN 1923799 A deals with a process for recovering ortho-aminobenzoic acid from mother liquor or wastewater, without giving more specific details of the origin thereof. The recovery is achieved by adsorption to a mildly basic resin or a macroporous resin. After adsorption has been achieved, the adsorption column is flushed with 2 to 6% sodium hydroxide solution to obtain an aqueous solution of sodium ortho-aminobenzoate.

FR 1.539.529 deals with obtaining high-purity aromatic carboxylic acids by sublimation. An example, among many, of a suitable carboxylic acid is meta-aminobenzoic acid.

The preparation of aminobenzoic acid by fermentation, which is the subject matter of the present invention, is also described in the literature. For the preparation of aminobenzoic acid by fermentation, reference is made by way of example to Balderas-Hemandez, V. E. et al., "Metabolic engineering for improving anthranilate synthesis from glucose in *Escherichia coli*", *Microb. Cell. Fact.* 2009, 8, 19 (doi: 10.118611475-2859-8-19). The patent literature, too, has publications in relation to this. For instance, the application US 2014/0371418 A1 claims recombinant microbacterial host cells which are capable of biologically converting a fermentable carbon-containing compound into para-aminobenzoic acid. Further examples of fermentation processes can be found in the applications WO 2015/124686 A1 and WO 2015/124687 A1 as well as in the literature cited in both applications. Fermentation processes generally proceed in an aqueous medium and in the case of preparation of aminobenzoic acid generally afford aqueous solutions (fermentation broths) with a content by mass of aminobenzoic acid in the range from 10.0 g/L to 100 g/L.

Besides the preparation of aminobenzoic acid by fermentation, WO 2015/124686 A1 and WO 2015/124687 A1 also deal with the subsequent decarboxylation thereof to give aniline. According to the teaching in these documents, the starting material aminobenzoic acid is isolated from the fermentation broth especially by crystallization and filtration. WO 2015/124687 A1 further discloses a preferred embodiment in which the mother liquor obtained in the crystallization procedure (having a residual concentration of aminobenzoic acid that is in line with the solubility of aminobenzoic acid under the particular conditions) is worked up in order to obtain further aminobenzoic acid. This is done through a sequence composed of an adsorption and a desorption step. The aminobenzoic acid-enriched desorbate obtained is recycled into the crystallization procedure. Yield losses are thus reduced. The adsorption is done on zeolites or activated carbon, and the desorption is done with water of a pH in the range from 5 to 10 or, alternatively, with organic solvents, especially 1-dodecanol. However, the desorption at the stated pH values has the disadvantage, when recycling into the crystallization procedure, that—especially in the upper part of the stated pH range—the amount of acid required for crystallization rises. The use of an organic solvent extraneous to the system is disadvantageous in principle, since associated with additional costs and increased disposal expenditure.

D. O. Cooney and J. Wijaya describe, in *Effect of pH and Added Salts on the Adsorption of Ionizable Organic Species onto Activated Carbon from Aqueous Solutions* (published in *Proceedings of the Second Engineering Foundation Conference on Fundamentals of Adsorption*, May 4-9 1986, Santa Barbara, Calif.) on pages 185 to 194, influencing the adsorption of ortho-aminobenzoic acid on activated carbon at various pH values with and without addition of NaCl. The adsorption maximum is at the isoelectric point. The adsorption at high pH values can be increased by addition of sodium chloride. For the experiments, laboratory chemicals were used. The peculiarities of ortho-aminobenzoic acid prepared by fermentation are not the subject matter of this publication; in particular, the use of a fermentation broth as starting material for the adsorption is not disclosed.

SUMMARY

Further improvements in the preparation of aminobenzoic acid or aminobenzoic acid conversion products prepared by fermentation would therefore be desirable. In particular, it would be desirable for the aminobenzoic acid initially arising in dissolved form in the known fermentation-based preparation processes to be isolated with minimal yield losses. At the same time, the process should be as simple as possible and be able to be designed without the use of solvents extraneous to the system (such as 1-dodecanol) in order to increase the economic viability of the process and to thus make the use thereof in industrial-scale production more attractive. Furthermore, it would be desirable to improve the isolation of the aminobenzoic acid (and thus the yield) without causing disadvantages as a result at another point in the overall process (as is the case, for example, in the desorption in the pH range of 5 to 10 as outlined in WO 2015/124687 A1).

Taking into account of what has been stated above, the present invention provides a process for preparing aminobenzoic acid or an aminobenzoic acid conversion product, comprising the following steps:
(I) providing an aqueous solution of aminobenzoic acid using a fermentation process;
(II) treating the aqueous solution of aminobenzoic acid, as provided in step (I), with an adsorbent, preferably activated carbon, to load the adsorbent with aminobenzoic acid and to obtain an aminobenzoic acid-depleted material;
(III) treating the aminobenzoic acid-loaded adsorbent from step (II) with an aqueous desorbent of a pH in the range from −0.8 to 3.0, preferably −0.5 to 3.0, particularly preferably 0.1 to 3.0, very preferably 0.5 to 2.5 and extremely very particularly preferably 1.0 to 2.0, to obtain an aminobenzoic acid-enriched desorbate and an aminobenzoic acid-depleted adsorbent;
(IV) obtaining the aminobenzoic acid from the desorbate obtained in step (III);
(V) optionally further reacting the aminobenzoic acid obtained in step (IV) to give an aminobenzoic acid conversion product, step (V) comprising in particular one of the following reactions:
(V-1) decarboxylating the aminobenzoic acid to give aniline;
(V-2) decarboxylating the aminobenzoic acid to give aniline, followed by acid-catalyzed reaction of the aniline with formaldehyde to form di- and polyamines of the diphenylmethane series;
(V-3) decarboxylating the aminobenzoic acid to give aniline, followed by acid-catalyzed reaction of the aniline with formaldehyde to form di- and polyamines of the diphenylmethane series, followed by reaction with phosgene to form di- and polyisocyanates of the diphenylmethane series;
(V-4) decarboxylating the aminobenzoic acid to give aniline, followed by reaction of the aniline to give an azo compound;
(V-5) reacting the aminobenzoic acid to give an amide;
(V-6) reacting the aminobenzoic acid to give conductive polymers such as, in particular, polyanthranilic acid.

DETAILED DESCRIPTION

In the context of the present invention, the term "aminobenzoic acid conversion product" refers to a product obtained by further chemical conversion of aminobenzoic acid.

It was found that, completely surprisingly, it is possible and even advantageous to carry out the desorption (step III) in a highly acidic aqueous medium, in contrast to what the person skilled in the art would derive from the teaching in WO 2015/124687 A1. Thus, obtaining the aminobenzoic acid from the desorbate is simplified, especially when this step comprises a crystallization procedure.

Embodiments of the invention are described in detail hereinafter. Various embodiments can be freely combined here with one another, unless the opposite is apparent to the person skilled in the art from the overall context.

There follows firstly a brief summary of various possible embodiments.

In a first embodiment of the invention, the process according to the invention comprises the following steps in step (I):
(I-1) fermenting a raw material comprising at least
a fermentable carbon-containing compound, preferably selected from the group consisting of starch hydrolysate, sugar cane juice, sugar beet juice and hydrolysates of lignocellulose-containing raw materials, and
a nitrogen-containing compound, preferably selected from the group consisting of ammonia gas, ammonia water, ammonium salts (especially ammonium sulfate and ammonium chloride) and urea,
in a fermentation reactor using microorganisms to obtain a fermentation broth; optionally followed by (I-2) a work-up comprising the following work-up steps:
(α) removing the microorganism from the fermentation broth obtained in step (I-1)
and/or
(β) decolorizing the fermentation broth obtained in step (I-1) or, when carrying out step (α), the microorganism-depleted fermentation broth obtained in step (α).

In a second embodiment of the invention, which is a preferred embodiment of the first embodiment, the aqueous solution of aminobenzoic acid that is used in step (II) is the fermentation broth obtained in step (I-1) or the one obtained in step (I-2), step (III) being carried out such that the concentration of aminobenzoic acid is higher in the desorbate than in the fermentation broth used in step (II) as aqueous solution of aminobenzoic acid.

In a third embodiment of the invention, which is a preferred configuration of the second embodiment, obtaining the aminobenzoic acid in step (IV) is achieved by (IV-1) guiding the aminobenzoic acid-enriched desorbate obtained in step (III) into a reactor in which aminobenzoic acid is precipitated by mixing with an aqueous solution of a pH higher than the pH of the aminobenzoic acid-enriched desorbate introduced into the reactor, the pH of the resulting mixture being preferably adjusted to a value in the range from 3.0 to 4.7, particularly preferably in the range from 3.2 to 3.7 and very particularly preferably in the range from 3.4 to 3.6;
(IV-2) removing the aminobenzoic acid precipitated in step (IV-1), preferably by filtration;
(IV-3) optionally further purifying the aminobenzoic acid removed in step (IV-2), preferably by washing with water.

In a fourth embodiment of the invention, which is a preferred configuration of the third embodiment, the aqueous solution used in step (IV-1) of a pH higher than the pH of the aminobenzoic acid-enriched desorbate introduced into the reactor is selected from the group consisting of ammonia water, sodium hydroxide solution, potassium hydroxide solution and calcium hydroxide solution.

In a fifth embodiment of the invention, which is a preferred configuration of the first embodiment, step (I) further comprises:

(I-3) introducing the fermentation broth obtained in step (I-1) or, if carried out, in step (I-2) into a reactor in which aminobenzoic acid is precipitated by mixing with an acidic aqueous solution, the pH of the resulting mixture being preferably adjusted to a value in the range from 3.0 to 4.7, preferably in the range from 3.2 to 3.7 and particularly preferably in the range from 3.4 to 3.6;
(I-4) removing the aminobenzoic acid precipitated in step (I-3), preferably by filtration, to obtain an aminobenzoic acid-depleted mother liquor;
(I-5) optionally further purifying the aminobenzoic acid removed in step (I-4), preferably by washing with water;
the aqueous solution of aminobenzoic acid that is used in step (II) being the aminobenzoic acid-depleted mother liquor obtained in step (I-4).

In a sixth embodiment of the invention, which is a preferred configuration of the fifth embodiment, the aminobenzoic acid-enriched desorbate obtained in step (III) is used as constituent of the acidic aqueous solution used in step (I-3), optionally together with an acid selected from the group consisting of hydrochloric acid, sulfuric acid, phosphoric acid and mixtures thereof, especially optionally together with hydrochloric acid of a concentration of from 15% by mass to 37% by mass.

In a seventh embodiment, which is another preferred configuration of the fifth embodiment, the acidic aqueous solution used in step (I-3) does not comprise aminobenzoic acid-enriched desorbate from step (III), but comprises instead an acid selected from the group consisting of hydrochloric acid, sulfuric acid, phosphoric acid and mixtures thereof, especially hydrochloric acid of a concentration of from 15% by mass to 37% by mass.

In an eighth embodiment, the acidic aqueous solution used in step (I-3) consists of one of the aforementioned acids of the seventh embodiment (i.e. no further acids are used).

In a ninth embodiment, which is a preferred configuration of the eighth embodiment, obtaining the aminobenzoic acid in step (IV) is achieved by (IV-1) guiding the aminobenzoic acid-enriched desorbate obtained in step (III) into a reactor in which aminobenzoic acid is precipitated by mixing with an aqueous solution of a pH higher than the pH of the aminobenzoic acid-enriched desorbate introduced into the reactor, the pH of the resulting mixture being preferably adjusted to a value in the range from 3.0 to 4.7, particularly preferably in the range from 3.2 to 3.7 and very particularly preferably in the range from 3.4 to 3.6;
(IV-2) removing the aminobenzoic acid precipitated in step (IV-1), preferably by filtration;
(IV-3) optionally further purifying the aminobenzoic acid removed in step (IV-2), preferably by washing with water.

In a tenth embodiment, which can be combined with all the other embodiments of the invention, the pH of the aqueous desorbent is kept constant while step (III) is carried out.

In an eleventh embodiment, which can be combined with all the other embodiments of the invention with the exception of the tenth embodiment, the pH of the aqueous desorbent passes through a gradient while step (III) is carried out.

In a twelfth embodiment, which can be combined with all the other embodiments of the invention, an aqueous solution of the ortho-isomer of aminobenzoate and/or of aminobenzoic acid is provided in step (I).

In a thirteenth embodiment, which can be combined with all the other embodiments of the invention, step (I) is carried out such that the provided aqueous solution of aminobenzoic acid has a pH in the range from 5.0 to 8.0.

In a fourteenth embodiment, which can be combined with all the other embodiments of the invention in which step (I-1) is carried out, the microorganisms used in step (I-1) comprise a species selected from the group consisting of *Escherichia coli, Pseudomonas putida, Corynebacterium glutamicum, Ashbya gossypii, Pichia pastoris, Hansenula polymorpha, Yarrowia lipolytica, Zygosaccharomyces bailii* and *Saccharomyces cerevisiae* and preferably only consist of representatives of precisely one of said species, *Corynebacterium glutamicum* ATTC 13032 being very particularly preferred.

The embodiments briefly outlined above and further possible configurations of the invention are elucidated in detail hereinafter:

Step (I) of the process according to the invention provides an aqueous solution of aminobenzoic acid using a fermentation process (fermentation step).

Aminobenzoic acid occurs in three isomeric forms (ortho-, meta- and para-aminobenzoic acid). In principle, the process according to the invention can be applied to all three isomers, either in isomerically pure form or as mixtures of different isomers. For all the embodiments of the present invention, it is preferred that the aminobenzoic acid to be provided in step (I) comprises the ortho-isomer. Particularly preferably, the aminobenzoic acid to be provided in step (I) comprises at least 50.0 mol %, very particularly preferably at least 90.0 mol %, of the ortho-isomer, based on the total molar amount of all aminobenzoic acid isomers present. Extremely very particularly preferably, the aminobenzoic acid to be provided in step (I) consists of the ortho-isomer in isomerically pure form (i.e. isomeric purity>99.0 mol %).

According to the invention, the aminobenzoic acid to be provided in step (I) is prepared by fermentation. Depending on the pH at which the fermentation is carried out, aminobenzoic acid does not occur in electroneutral form in step (I), but instead as aminobenzoate for example (this is, however, irrelevant to the type of isomer formed). In the context of this invention, the language in step (I) is simplified by the constant reference to aminobenzoic acid, this being understood to mean that the cationic [i.e. diprotonated], anionic [i.e. deprotonated] and neutral [i.e. electroneutral] form of aminobenzoic acid are encompassed, unless something else arises from the boundary conditions. Particularly preferably, step (I) is carried out such that the provided aqueous solution of aminobenzoic acid has a pH in the range from 5.0 to 8.0. In this case, the aminobenzoic acid is—depending on whether the fermentation is carried out in the lower or in the upper range of the stated pH range—present in neutral form (i.e. as aminobenzoic acid "in the narrower sense") and/or as anion (i.e. as aminobenzoate). In this connection, the term "aminobenzoic acid in neutral form" (aminobenzoic acid "in the narrower sense") self-evidently encompasses not only the structure $H_2N$—$(C_6H_4)$—$COOH$, but also the so-called "zwitterion" $H_3N^+$—$(C_6H_4)$—$COO^-$, which can be present as (electro)neutral aminobenzoic acid. Particular preference is given to a pH range from 6.5 to 8.0; here, the aminobenzoic acid is predominantly to entirely present as anion.

In a preferred configuration of the invention, step (I) comprises the following step (I-1):
 (I-1) fermenting a raw material comprising at least
  a fermentable carbon-containing compound, preferably selected from the group consisting of starch hydrolysate, sugar cane juice, sugar beet juice and hydrolysates of lignocellulose-containing raw materials, and
  a nitrogen-containing compound, preferably selected from the group consisting of ammonia gas, ammonia water, ammonium salts (especially ammonium sulfate and ammonium chloride) and urea,
  in a fermentation reactor using microorganisms to obtain a fermentation broth.

Step (I-1) of the process according to the invention can be carried out by any procedure known from the prior art.

Preferred microorganisms for carrying out step (I-1) are bacteria or fungi, especially yeasts. In this connection, particular preference is given to microorganisms of a species selected from the group consisting of *Escherichia coli, Pseudomonas putida, Corynebacterium glutamicum, Ashbya gossypii, Pichia pastoris, Hansenula polymorpha, Yarrowia lipolytica, Zygosaccharomyces bailii* and *Saccharomyces cerevisiae*. Very particularly preferably, the microorganisms used in step (I-1) only consist of representatives of precisely one of said species, *Corynebacterium glutamicum* ATTC 13032 being extremely very particularly preferred. The pH to be maintained in the fermentation is based on the microorganism used. Microorganisms such as *Corynebacterium glutamicum, Pseudomonas putida* or *Escherichia coli* are preferably cultured at neutral pH (i.e. at a pH in the range from 6.0 to 8.0). Microorganisms such as *Saccharomyces cerevisiae* in contrast are preferably cultured in acidic medium (i.e. at a pH in the range from 4.0 to 5.0).

In each case, the microorganism of step (I-1) is preferably selected such that the ortho-isomer of aminobenzoic acid is formed in the fermentation.

In a preferred configuration of the invention, bacteria are used as microorganisms. In this connection, reference is made in particular to patent applications WO 2015/124686 A1 and WO 2015/124687 A1, which describe a fermentation usable according to the invention with use of bacteria (see, for example, WO 2015/124687 A1, (i) page 15, line 8 to page 16, line 30, (ii) example 1 (page 29, lines 4 to 26), (iii) example 3 (especially page 34, lines 10 to 18), (iv) example 4 (especially page 55, lines 9 to 31). In particular, bacteria are used which are capable of converting a fermentable carbon-containing compound into aminobenzoic acid in the presence of a suitable nitrogen source without the aminobenzoic acid thus formed being consumed straightaway in intracellular biochemical processes, with the result that aminobenzoic acid is enriched in the cell and ultimately passes into the fermentation broth.

In another preferred configuration of the invention, yeasts are used as microorganisms. In this connection, reference is made in particular to international patent application WO 2017/102853 A1. In particular, yeast cells are used which are capable of converting a fermentable carbon-containing compound into aminobenzoic acid in the presence of a suitable nitrogen source without the aminobenzoic acid thus formed being consumed straightaway in intracellular biochemical processes, with the result that aminobenzoic acid is enriched in the cell and ultimately passes into the fermentation broth.

Two routes are available in principle for obtaining a bacterium of this kind or a yeast of this kind, which routes can also be combined in a preferred configuration:
 (i) The enzymatic reactions in the aminobenzoic acid metabolic pathway of the bacterial cell or yeast cell can be increased such that aminobenzoic acid is produced more rapidly than it is consumed.
 (ii) The conversion reactions which convert aminobenzoic acid into further metabolites or products (e.g. tryptophan) can be reduced or switched off, with the result that even the rate of aminobenzoic acid formation in wild-type strains is sufficient to lead to an enrichment of aminobenzoic acid in the cell.

Methods for obtaining bacteria or yeast cells with the properties specified above are known from the prior art. Suitable bacteria or yeast cells can be identified, for example, by screening for mutants which secrete aminobenzoic acid into the surrounding medium. The targeted modification of key enzymes by means of genetic engineering methods is preferred however. Using customary genetic engineering methods, gene expression and enzyme activity can be enhanced, reduced or even completely suppressed as desired. Recombinant strains are the result.

Particularly preferably, the bacteria or yeast cells which are capable of converting a fermentable carbon-containing compound into aminobenzoic acid in the presence of a nitrogen-containing compound contain a modification to the anthranilate phosphoribosyltransferase activity, which decreases said enzyme activity. As a result of said modification, the conversion of ortho-aminobenzoate into N-(5-phospho-D-ribosyl)anthranilate is reduced or completely suppressed. This causes an enrichment of aminobenzoic acid in the cell. The expression "anthranilate phosphoribosyltransferase activity" refers, in this connection, to an enzyme activity which catalyzes the conversion of ortho-aminobenzoate into N-(5-phospho-D-ribosyl)anthranilate.

In yeasts, anthranilate phosphoribosyltransferase activity is genetically encoded by the native gene TRP4 (YDR354W). In the bacterium *Corynebacterium glutamicum*, anthranilate phosphoribosyltransferase activity is encoded by the trpD gene (cg3361, Cg13032, NCg12929). In the case of *Pseudomonas putida*, the encoding is effected via the trpD gene (PP_0421) within the trpDC operon.

The described decrease in anthranilate phosphoribosyltransferase activity can be achieved in principle in three ways:
  (i) The regulation of the expression of the gene for anthranilate phosphoribosyltransferase activity can be modified such that the transcription of the gene or subsequent translation is reduced or suppressed.
  (ii) The nucleic acid sequence of the gene for anthranilate phosphoribosyltransferase activity can be modified such that the enzyme which is encoded by the modified gene has a lower specific activity.
  (iii) The native gene for anthranilate phosphoribosyltransferase activity can be replaced with a different gene which originates from a different organism and encodes an enzyme having a specific anthranilate phosphoribosyltransferase activity lower than that of the native genes mentioned above (e.g. TRP4, trpD or trpDC).

Irrespective of which microorganism is used, the fermentation broth at the start of the fermentation in step (I-1) comprises recombinant cells of the microorganism used and at least a fermentable carbon-containing compound (and at least a nitrogen-containing compound as nitrogen source). Preferably, the fermentation broth additionally contains further constituents selected from the group consisting of buffer systems, inorganic nutrients, amino acids, vitamins and further organic compounds which are required for the growth or housekeeping metabolism of the recombinant cells. The fermentation broth is water-based. After the fermentation process has been started, the fermentation broth also comprises aminobenzoic acid, the fermentation product which is striven for.

A fermentable carbon-containing compound in the context of the present invention is understood to mean any organic compound or mixture of organic compounds that can be used to produce aminobenzoic acid by the recombinant cells of the microorganism used. The production of aminobenzoic acid can take place in this case in the presence or in the absence of oxygen.

Preference is given in this connection to those fermentable carbon-containing compounds which can additionally serve as energy and carbon source for the growth of the recombinant cells of the microorganism used. Particularly suitable are starch hydrolysate, sugar cane juice, sugar beet juice and hydrolysates of lignocellulose-containing raw materials. Likewise suitable are glycerol and C1 compounds, especially carbon monoxide.

In a preferred embodiment, step (I-1) is carried out continuously, i.e. the reactants are fed continuously to the fermentation reactor and the product is withdrawn continuously from the fermentation reactor. In a continuous process regime, the microorganism may be discharged with the product stream; however, since the microorganism generally reproduces itself, feeding fresh microorganism is generally unnecessary (but can of course be done if required). Cell retention to avoid discharge of microorganism is also possible.

In another preferred embodiment, step (I-1) is carried out in a discontinuous process regime (so-called "batch mode"). In one variant of the discontinuous mode of operation (so-called "fed-batch mode"), the reactants are fed continuously to the fermentation reactor as long as the reactor volume allows it without products being withdrawn from the reactor. The reaction is interrupted after addition of the maximum possible amount of reactants and the product mixture is withdrawn from the fermentation reactor.

Irrespective of the exact mode of operation, the fermentation reactor preferably comprises devices for measuring important process parameters such as temperature, pH of the fermentation broth, concentration of substrate and product, dissolved oxygen content, and cell density of the fermentation broth. In particular, the fermentation reactor preferably comprises devices for adjusting at least one (preferably all) of the aforementioned process parameters.

Suitable fermentation reactors are stirred tanks, membrane reactors, plug flow reactors or loop reactors (see for example Bioprozesstechnik, Horst Chmiel, ISBN-10: 3827424763, Spektrum Akademischer Verlag). Particularly preferred for both aerobic and anaerobic fermentations are stirred tank reactors and loop reactors (particularly airlift reactors in which circulation of the liquid in the reactor is achieved by sparging).

Preferably, step (I) comprises not only step (I-1), but also a work-up of the fermentation broth obtained in a step (I-2). Said work-up preferably comprises the following steps:
(α) removing the microorganism from the fermentation broth obtained in step (I-1)
and/or
(β) decolorizing the fermentation broth obtained in step (I-1) or, when carrying out step (α), the microorganism-depleted fermentation broth obtained in step (α).

Removing the microorganism from the fermentation broth in step (α) is known per se from the prior art and is effected in the context of the present invention particularly by filtration, settling, separation in hydrocyclones or centrifugation. One possible configuration of this step is described in WO 2015/124686 A1 and WO 2015/124687 A1. In this connection, reference is made to WO 2015/124687 A1, page 15, line 8 to page 15, line 17.

Irrespective of whether the microorganism is removed or not, step (I-2) can, if required, comprise a step (β) for decolorizing the fermentation broth or the microorganism-depleted fermentation broth. In one embodiment, said step (β) is preferably carried out such that fermentation broth or microorganism-depleted fermentation broth is passed through a column with solid packing in order to remove colorants by means of adsorption. A possible solid phase which can be used is, for example, kieselguhr, activated carbon or ion-exchange packing. This embodiment is especially preferred when step (α) is carried out. In another embodiment, the fermentation broth obtained in step (I-1) is stirred while pulverulent activated carbon or pulverulent kieselguhr is added and it is then filtered.

Step (β) is preferably carried out when the fermentation broth or the microorganism-depleted fermentation broth from step (α) contains colored substances of the kind which could interfere with the subsequent steps of the process according to the invention, especially the crystallization which is carried out in preferred embodiments and will be described in detail.

The invention can be realized in different variants, which will be described in detail further below. Depending on the variant, the aqueous solution from the fermentation in step (I) is further treated differently. Irrespective thereof, there are, with regard to steps (II) and (III), preferred embodiments common to all variants, which embodiments shall be described first of all.

In step (II), what takes place is the adsorption of the aqueous solution of aminobenzoic acid provided in step (I) (adsorption step).

In all variants, said adsorption is preferably done at a pH in the range from >3.0 to 4.0, particularly preferably in the range from 3.3 to 3.7 and very particularly preferably at pH 3.5. The temperature is preferably in the range from 15° C. to 40° C., particularly preferably in the range from 15° C. to 35° C. and very particularly preferably in the range from 20° C. to 25° C. The adsorption is preferably done on activated carbon as adsorbent. Suitable adsorption apparatuses are in particular columns, expediently laboratory-scale chromatography columns, with which the adsorbent is loaded, especially in the form of an adsorber bed.

In step (III), what takes place is the desorption of the aminobenzoic acid adsorbed in step (II) (desorption step).

In all variants, the desorption is done at a pH in the range from −0.8 to 3.0, preferably −0.5 to 3.0, particularly preferably 0.1 to 3.0, very particularly preferably in the range from 0.5 to 2.5 and extremely very particularly preferably in the range from 1.0 to 2.0 (i.e. the desorbent used has—at 20° C. —a pH in the stated ranges). This means that the desorption of the majority of the aminobenzoic acid (i.e. at least 90%, preferably 95% and in particular >99% of the total amount of aminobenzoic acid adsorbed in step (II)) is done in these pH ranges. This does not encompass a desorption of the majority of the aminobenzoic acid at other pH values, followed by an acidic wash of the adsorbent in the stated pH ranges. Especially suitable as aqueous desorbent is an acidic aqueous solution, especially hydrochloric acid [HCl(aq)]. Preferably, the loaded adsorbent remains in the apparatus used for the adsorption (especially a column) in the desorption step. In industrial-scale production, at least two adsorbent-loaded columns, in which steps (III) and (IV) are carried out in alternation, are preferably kept available to this end.

In a first embodiment, the aqueous desorbent is guided through the column used in the adsorption step in the opposite direction to the aqueous solution of aminobenzoic acid beforehand. When the aminobenzoic acid concentration determined in the desorbate reaches a minimum (i e does not sink any further), the supply of the aqueous desorbent is stopped. On a laboratory scale, concentration determination is achieved via regular sampling and analysis, preferably by means of liquid chromatography with UV detector. In an industrial process, UV online analyzers can be used.

Thereafter, any desorbate still present in the adsorbent (in the adsorber bed) is eluted, preferably with water (especially with demineralized water), fermentation broth or mother liquor from the crystallization (additionally described in detail further below), preferably fermentation broth or mother liquor from the crystallization. This is preferably done at a temperature in the range from 15° C. to 40° C., particularly preferably in the range from 15° C. to 35° C. and very particularly preferably in the range from 20° C. to 25° C. Thereafter, the adsorber bed is preferably flushed, preferably with water (especially with demineralized water), fermentation broth or mother liquor from the crystallization, preferably fermentation broth or mother liquor from the crystallization, likewise at a temperature in the range from 15° C. to 40° C., particularly preferably in the range from 15° C. to 35° C. and very particularly preferably in the range from 20° C. to 25° C. The flush liquid obtained can be discarded or—preferably—recycled into the process, specifically such that the flush liquid is supplied to the adsorption step (II) together with the aqueous solution of aminobenzoic acid. As an alternative to the described flushing, it is also possible to circulate water (especially with demineralized water), fermentation broth or mother liquor from the crystallization, preferably fermentation broth or mother liquor from the crystallization, through the adsorber bed and, while doing so, to meter in an aqueous base solution (preferably selected from the group consisting of ammonia water, sodium hydroxide solution, potassium hydroxide solution and calcium hydroxide solution, especially sodium hydroxide solution) until the pH striven for (which is preferably in the range from >3.0 to 4.0, particularly preferably in the range from 3.3 to 3.7 and very particularly preferably at pH 3.5) for the adsorption step (II) is reached.

In another embodiment, the desorbate is circulated through the adsorbent-loaded column until equilibrium is reached. Equilibrium is reached when the aminobenzoic acid concentration measured in the desorbate reaches a maximum, i.e. assumes the value which can be maximally reached for the chosen desorbent amount and the present degree of loading of the adsorbent. On a laboratory scale, concentration determination is achieved via regular sampling and analysis, preferably by means of liquid chromatography with UV detector. In an industrial process, UV online analyzers can be used. The elution of the desorbate present in the adsorbent is preferably done as described above for the first embodiment.

In all embodiments, the temperature in the desorption step is preferably in the range from 50° C. to 90° C., particularly preferably in the range from 60° C. to 85° C. and very particularly preferably in the range from 70° C. to 80° C. Owing to the low pH, the aminobenzoic acid is desorbed in cationic (protonated) form.

The variants of the invention that have already been mentioned are now elucidated in detail hereinafter.

It is possible to supply directly to step (II) the aqueous solution of aminobenzoic acid obtained by fermentation in the manner outlined further above. In this first variant of the invention, the sequence of adsorption (step (II)) and desorption (step (III)) serves to concentrate the aqueous solution of aminobenzoic acid in order to make it easier to carry out step (IV)—obtaining the aminobenzoic acid. In the context of this variant, the starting material used for carrying out step (II) is in particular the fermentation broth obtained in step (I-1) or—if carried out—the one obtained in step (I-2), i.e. in the terminology of the present invention, the aqueous solution of aminobenzoic acid that is used in step (II) is, in this embodiment, the fermentation broth obtained in step (I-1) or the one obtained in step (I-2). What is essential in said variant is that step (III) is carried out such that the concentration of aminobenzoic acid is higher in the desorbate than in the fermentation broth used in step (II) as aqueous solution of aminobenzoic acid. To this end, the procedure is carried out such that the volume of aqueous desorbent used in total in step (III) is lower than the total volume of the aqueous solution of aminobenzoic acid that was treated in step (II).

In said variant, obtaining the aminobenzoic acid in step (IV) is achieved especially by (IV-1) guiding the aminobenzoic acid-enriched (highly acidic—pH in the range from −0.8 to 3.0, preferably −0.5 to 3.0, particularly preferably 0.1 to 3.0, very particularly preferably 0.5 to 2.5 and extremely very particularly preferably 1.0 to 2.0) desorbate obtained in step (III) into a reactor in which aminobenzoic acid is precipitated by mixing with an aqueous solution of a pH higher than the pH of the aminobenzoic acid-enriched desorbate introduced into the reactor, the pH of the resulting mixture being preferably adjusted to a value in the range from 3.0 to 4.7, preferably in the range from 3.2 to 3.7 and particularly preferably in the range from 3.4 to 3.6 (crystallization);

(IV-2) removing the aminobenzoic acid precipitated in step (IV-1), preferably by filtration;

(IV-3) optionally further purifying the aminobenzoic acid removed in step (IV-2), preferably by washing with water.

In this connection, the aqueous solution used in step (IV-1) of a pH higher than the pH of the aminobenzoic acid-enriched desorbate introduced into the reactor is preferably selected from the group consisting of ammonia water, sodium hydroxide solution, potassium hydroxide solution and calcium hydroxide solution. In said variant, the crystallization is thus a component of step (IV) of the invention.

However, preference is given—this is the subject matter of a second variant of the invention—to carrying out the crystallization after step (I-1) or—if carried out—step (I-2). In this configuration, the invention thus encompasses a process in which step (I) further comprises:

(I-3) introducing the fermentation broth obtained in step (I-1) or, if carried out, in step (I-2) into a reactor in which aminobenzoic acid is precipitated by mixing with an acidic aqueous solution, the pH of the resulting mixture being preferably adjusted to a value in the range from 3.0 to 4.7, preferably in the range from 3.2 to 3.7 and particularly preferably in the range from 3.4 to 3.6;

(I-4) removing the aminobenzoic acid precipitated in step (I-3), preferably by filtration, to obtain an aminobenzoic acid-depleted mother liquor;

(I-5) optionally further purifying the aminobenzoic acid removed in step (I-4), preferably by washing with water.

The aqueous solution of aminobenzoic acid that is used in step (II) is then the aminobenzoic acid-depleted mother liquor obtained in step (I-4). In said variant, the sequence of adsorption (step (II)) and desorption (step (III)) thus serves to further deplete the mother liquor obtained in the crystallization (here: step (I-3)) of aminobenzoic acid dissolved therein and to thus increase the yield.

Since, in said variant, the crystallization is initiated by addition of acid (step (I-3)), it is possible and preferred to use the aminobenzoic acid-enriched desorbate (which is highly acidic—pH in the range from −0.8 to 3.0, preferably −0.5 to 3.0, particularly preferably 0.1 to 3.0, very particularly preferably 0.5 to 2.5 and extremely very particularly preferably 1.0 to 2.0) obtained in step (III) as a constituent, possibly as sole constituent, of the acidic aqueous solution used in step (I-3). In this configuration of the second variant, the aminobenzoic acid is thus—as in variant 1—obtained by crystallization from the desorbate, but with the difference that, in this case, the aminobenzoic acid to be obtained from the desorbate is part of the precipitant (the acidic aqueous solution that is added). In this configuration of the second variant, step (IV)—obtaining the aminobenzoic acid from the desorbate—therefore corresponds to step (I-3).

It is also possible to use additionally an acid from an external source for the precipitation in step (I-3), preferably hydrochloric acid, sulfuric acid and/or phosphoric acid, especially hydrochloric acid of a concentration of from 15% by mass to 37% by mass. Said acid from an external source is then a constituent of the acidic aqueous solution in addition to the desorbate already mentioned. Further acids are preferably not used.

Said acid from an external source can, however, also be used alone as acidic aqueous solution. In this case, it is then preferred, obtaining aminobenzoic acid from the acidic desorbate, to precipitate aminobenzoic acid by mixing with an aqueous solution of a pH higher than the pH of the aminobenzoic acid-enriched desorbate, the pH of the resulting mixture being preferably adjusted to a value in the range from 3.0 to 4.7, preferably in the range from 3.2 to 3.7 and particularly preferably in the range from 3.4 to 3.6, and the aqueous solution of a pH higher than the pH of the aminobenzoic acid-enriched desorbate being preferably selected from the group consisting of ammonia water, sodium hydroxide solution, potassium hydroxide solution and calcium hydroxide solution. Work-up steps corresponding to steps (I-4) and (I-5) follow. In this embodiment too, obtaining the aminobenzoic acid from the desorbate from step (III) is thus done by crystallization; however—as in variant 1—a precipitant of a higher pH is added to the desorbate. In this configuration of the second variant, step (IV), obtaining aminobenzoic acid from the acidic desorbate, is therefore, as in the first variant, its own step, which is however, in contrast to the first variant, different from the "actual" crystallization (the crystallization of the majority of the aminobenzoic acid; in this case in step (1-3)). Since this configuration of the second variant requires two crystallization steps, it is less preferred than the one outlined at the beginning.

Irrespective of which variant of the invention is realized in which configuration, there are preferred embodiments for the crystallization step, which embodiments are described in detail below.

In a first step (corresponding to step (IV-1) or (I-3)) of the crystallization itself, the pH is adjusted by addition of acid or base (dependent on the starting pH—see the description of the different variants and configurations above) to particular solution of aminobenzoic acid such that aminobenzoic acid (i.e. aminobenzoic acid in neutral form) crystallizes. This type of crystallization is also referred to as reactive crystallization. This is preferably done in such a way that the pH of the resulting mixture corresponds to, or at least approximates, the value of the isoelectric point of the aminobenzoic acid isomer to be precipitated. In the case of ortho-aminobenzoic acid as desired product, the pH is therefore preferably adjusted to a value in the range from 3.0 to 4.7, particularly preferably to a value in the range from 3.2 to 3.7 and very particularly preferably to a value in the range from 3.4 to 3.6, i.e. close to or corresponding to the isoelectric point at pH 3.5. For the other two isomers of aminobenzoic acid, said isoelectric point is about pH 3.7 in both cases. The pH adjustment in this step is preferably "one-step" in the sense that the desired target pH is directly adjusted by addition of acid or base without intermediate steps (such as filtration, centrifugation, column-chromatography treatment and the like) being carried out at pH values between the starting pH and the target pH.

Suitable as reactor for this step are customary configurations of chemical reactors that are familiar to the person skilled in the art. Examples include stirred tanks or forced circulation crystallizers such as those of the "Oslo type". The addition of the acid or base into the reactor is preferably done in a continuous manner. The process product of this step—i.e. aminobenzoic acid suspended in acidic mother liquor—is removed from the reactor at least in batches or, preferably, also in a continuous manner. In this case, the further treatment following step is preferably also done in batches or in a continuous manner.

In a second step (corresponding to step (IV-2) or (I-4)), the aminobenzoic acid precipitated in the previous step is removed. Methods for this purpose are known per se from the prior art. According to the invention, said step is preferably carried out by filtration or centrifugation. Preferably, said step is carried out as described in WO 2015/124687 A1. In this connection, reference is made to WO 2015/124687 A1, page 17, line 13 to page 17, line 16. Filtration can be carried out at reduced pressure, atmospheric pressure or elevated pressure. Centrifugation can be carried out using commercial centrifuges. It is also possible to leave the suspension obtained in the first step standing until the precipitated crystals of aminobenzoic acid settle out and to then decant or aspirate the supernatant mother liquor.

What follows in an optional third step (corresponding to step (IV-3) or (I-5)) is a further purification of the previously obtained aminobenzoic acid. Said step is also known per se from the prior art (see especially WO 2015/124687 A1 and in particular to WO 2015/124687 A1, page 18, line 4 to page 18, line 6) and is preferably achieved by one or more washes with aqueous wash media, especially water. In order to avoid yield losses, the pH of the aqueous wash medium can be adjusted to the same value in the first step after completion of addition of acid or base, i.e. in this embodiment, washing is carried out not with water, but with a diluted acid or diluted base, especially the same acid or base as used in the precipitation reagent.

Irrespective of which variant of the invention is realized in which configuration, the aminobenzoic acid is obtained in neutral form (i.e. as aminobenzoic acid "in the narrower sense") in step (IV). In said form, it can be directly supplied to the optional (and preferred) reaction to give an aminobenzoic acid conversion product in step (V). Selected further reactions of the aniline obtained in step (IV) are:

(V-1) decarboxylating the aminobenzoic acid to give aniline;

(V-2) decarboxylating the aminobenzoic acid to give aniline, followed by acid-catalyzed reaction of the aniline with formaldehyde to form di- and polyamines of the diphenylmethane series;

(V-3) decarboxylating the aminobenzoic acid to give aniline, followed by acid-catalyzed reaction of the aniline with formaldehyde to form di- and polyamines of the diphenylmethane series, followed by reaction with phosgene to form di- and polyisocyanates of the diphenylmethane series;

(V-4) decarboxylating the aminobenzoic acid to give aniline, followed by reaction of the aniline to give an azo compound;

(V-5) reacting the aminobenzoic acid to give an amide;

(V-6) reacting the aminobenzoic acid to give a conductive polymer such as, in particular, polyanthranilic acid.

Decarboxylating the aminobenzoic acid to give aniline (V-1) is known per se and can be carried out by any process from the prior art. Preference is given to the following procedure:

Step (V-I) can be carried out in all reactor types which are customary in process technology and familiar to the person skilled in the art, such as for example stirred tank reactors (preferably with fixed catalyst bed),
continuous stirred tank reactors (CSTR), especially continuous stirred tank reactors (CSTR) with fixed catalyst bed,
plug flow reactors with fixed catalyst bed or
slurry phase reactors (also called suspension reactors) with catalyst recirculation or catalyst recovery.

It is also possible to connect multiple reactors in series to give a reactor cascade, i.e. the liquid product discharge of one reactor flows into the next reactor for further completion of the conversion.

Step (V-I) is preferably carried out in the presence of a catalyst. Catalysts suitable for carrying out step (V-I) are catalysts familiar to the person skilled in the art, such as, for example, aqueous acids such as sulfuric acid, nitric acid and hydrochloric acid; solid acids such as zeolites and Si—Ti molecular sieves, solid bases such as hydroxyapatite and hydrotalcite; polymeric acids such as ion exchange resins (particularly Amberlyst). If the catalyst is used in the form of particles or in powder form, a preferred embodiment of the invention consists in slurrying the catalyst in the liquid reaction mixture, preferably by stirring. Particularly suitable for this purpose is a slurry phase reactor (also called suspension reactor), wherein the catalyst is used in a concentration in the range from 0.100% by mass to 50.0% by mass, preferably in the range from 10.0% by mass to 30.0% by mass, based on the total mass of the liquid reaction mixture. In another preferred embodiment, the catalyst is arranged in a catalyst bed in a tubular reactor, wherein the catalyst present particularly in particles (e.g. spheres) in this embodiment is preferably fixed in the catalyst bed, for example arranged between sieve plates. Irrespective of the type of reactor used, the catalyst used in step (I) is preferably a zeolite catalyst, particularly preferably a zeolite of type Y in protonated form (H form). The arrangement of the catalyst, present particularly in particle form, in a fixed bed is of course not restricted to tubular reactors, but can in principle also be applied to stirred reactors. Furthermore, it is possible to use the catalyst in monolithic form.

In the decarboxylation of step (V-I), the following reaction parameters can be observed for example:

temperature preferably in the range from 140° C. to 240° C. and pressure preferably in the range from 1.00 $bar_{(abs.)}$ to 20.0 $bar_{(abs.)}$, temperature particularly preferably in the range from 160° C. to 220° C. and pressure particularly preferably in the range from 1.00 $bar_{(abs.)}$ to 15.0 $bar_{(abs.)}$, temperature very particularly preferably at a temperature in the range from 180° C. to 200° C. and pressure very particularly preferably in the range from 4.00 $bar_{(abs.)}$ to 10.0 $bar_{(abs)}$.

The stream containing aniline, prior to its withdrawal from the reactor, preferably passes through a filter in order to prevent solid particles (e.g. catalyst particles) being entrained.

The aminobenzoic acid to be decarboxylated is preferably used in solution for carrying out step (V-1). Suitable solvents are water or organic solvents such as 1-dodecanol or aniline.

Step (V-I) is preferably carried out continuously, i.e. the aminobenzoic acid to be decarboxylated is fed continuously to the reactor and the product is withdrawn continuously from the reactor. In one variant of this procedure, at least some of the catalyst is also exchanged in the continuous operation, constantly or at intervals, in order to prevent its performance capacity from being exhausted. A discontinuous process regime (so-called "batch mode") is, however, also possible. In one variant of the discontinuous mode of operation (so-called "fed batch mode"), the reactants are fed continuously to the reactor as long as the reactor volume allows it without products being withdrawn from the reactor. The reaction is interrupted after addition of the maximum possible amount of reactants and the product mixture is withdrawn from the reactor.

In an alternative preferred embodiment, a process regime is also feasible in which aminobenzoic acid to be decarboxylated is fed continuously to the reactor and the product is withdrawn continuously from the reactor, but consumed catalyst is not withdrawn in the continuous operation and, instead, fresh catalyst is added (either constantly or at intervals) until the maximum catalyst amount predetermined by the available reactor volume has been reached in the reactor, and the reactor is then taken out of operation for the purposes of cleaning and catalyst exchange.

In all embodiments, preference is given to carrying out step (V-I) under exclusion of oxygen. To inertize the reactor, inert gases such as nitrogen, carbon dioxide or noble gases are suitable.

The crude aniline withdrawn from the reactor of step (V-1) is preferably purified before it is used further. This purification can be effected by processes familiar to the person skilled in the art. In particular, the purification includes at least one distillation step, upstream of which a water removal by phase separation can be effected. The purification may also include a base treatment for removing acidic impurities before, during or after the distillation step. Suitable configurations are, for example, described in EP-A-1 845 079, EP-A-1 845 080, EP-A-2 263 997 and EP-A-2 028 176. (These documents are concerned with the purification of aniline which has been obtained by hydrogenation of nitrobenzene; the described steps for purifying the crude aniline are, however, also applicable to aniline produced in other ways.)

Further reacting aniline thus obtained with formaldehyde to give di- and polyamines of the diphenylmethane series (V-2) is known per se and can be carried out by any process from the prior art. The continuous or partially discontinuous preparation of di- and polyamines of the diphenylmethane series from aniline and formaldehyde is, for example, disclosed in EP 1 616 890 A1, U.S. Pat. No. 5,286,760, EP-A-451442 and WO-A-99/40059. The reaction is effected under acid catalysis. Suitable as acidic catalyst is preferably hydrochloric acid.

Further reacting the di- and polyamines of the diphenylmethane series that are thus obtained with phosgene to give di- and polyisocyanates of the diphenylmethane series (V-3) is also known per se and can be carried out by any process from the prior art. Suitable processes are, for example, described in EP 2 077 150 B1, EP 1 616 857 A1, EP 1 873 142 A1, and EP 0 314 985 B1.

Reacting the aniline obtained by decarboxylating the aminobenzoic acid obtained according to the invention to give azo compounds, especially azo dyes (V-4) can be carried out by any process from the prior art. Reference may be made by way of example to the known preparation of aniline yellow (para-aminoazobenzene; CAS 493-5-7) or indigo (2,2'-bis(2,3-dihydro-3-oxomethylidene); CAS 482-89-3) (Per Wiklund et al., *Current Organic Synthesis*, 2006, 3, 379-402).

Reacting the aminobenzoic acid obtained according to the invention to give an amide (V-5) can be carried out by any process from the prior art. Mention may be made by way of example of the primary amine of anthranilic acid (2-aminobenzylamide), which is used inter alia as starting material for the preparation of pharmaceuticals (Per Wiklund et al., *Current Organic Synthesis*, 2006, 3, 379-402).

Reacting the aminobenzoic acid obtained according to the invention to give a conductive polymer such as, in particular, polyanthranilic acid (V-6) can be carried out by any process from the prior art. An example is described in Bhavana Guptaa et al., *Polymers Advanced Technologies*, 2011, 22, 1982-1988.

The invention claimed is:

1. A process for preparing aminobenzoic acid or an aminobenzoic acid conversion product, comprising:
    (I) providing an aqueous solution of aminobenzoic acid using a fermentation process, wherein step (I) comprises:
    (I-1) fermenting a raw material comprising:
        a fermentable carbon-containing compound, and
        a nitrogen-containing compound,
    in a fermentation reactor using microorganisms to obtain a fermentation broth; optionally followed by
    (I-2) a work-up comprising the following work-up steps:
    (α) removing the microorganism from the fermentation broth obtained in step (I-1) and/or
    (β) decolorizing the fermentation broth obtained in step (I-1) or, when carrying out step (α), the microorganism-depleted fermentation broth obtained in step (α);
    wherein step (I) further comprises:
    (I-3) introducing the fermentation broth obtained in step (I-1) or, if carried out, in step (I-2) into a reactor in which aminobenzoic acid is precipitated by mixing with an acidic aqueous solution, the pH of the resulting mixture being adjusted to a value in the range from 3.0 to 4.7; and
    (I-4) removing the aminobenzoic acid precipitated in step (I-3) to obtain an aminobenzoic acid-depleted mother liquor;
    (II) treating the aqueous solution of aminobenzoic acid, as provided in step (I), which is the aminobenzoic acid-depleted mother liquor obtained in step (I-4), with an adsorbent to load the adsorbent with aminobenzoic acid and to obtain an aminobenzoic acid-depleted material;
    (III) treating the aminobenzoic acid-loaded adsorbent from step (II) with an aqueous desorbent of a pH in the range from −0.8 to 3.0 to obtain an aminobenzoic acid-enriched desorbate and an aminobenzoic acid-depleted adsorbent;
    (IV) obtaining the aminobenzoic acid from the desorbate obtained in step (III) by using the aminobenzoic acid-enriched desorbate as a constituent of the acidic aqueous solution used in step (I-3); and
    (V) optionally further reacting the aminobenzoic acid obtained in step (IV) to give an aminobenzoic acid conversion product.

2. The process of claim 1, in which step (I) further comprises:
    (I-5) purifying the aminobenzoic acid removed in step (I-4).

3. The process of claim 1, in which the aminobenzoic acid-enriched desorbate obtained in step (III) is used as a constituent of the acidic aqueous solution used in step (I-3), together with an acid selected from the group consisting of hydrochloric acid, sulfuric acid, phosphoric acid and mixtures thereof.

4. The process of claim 1, in which the pH of the aqueous desorbent is kept constant while step (III) is carried out.

5. The process of claim 1, in which the pH of the aqueous desorbent passes through a gradient while step (III) is carried out.

6. The process of claim 1, in which an aqueous solution of the ortho-isomer of aminobenzoate and/or of aminobenzoic acid is provided in step (I).

7. The process of claim 1, in which the microorganisms used in step (I-1) comprise a species selected from the group consisting of *Escherichia coli, Pseudomonas putida, Corynebacterium glutamicum, Ashbya gossypii, Pichia pastoris, Hansenula polymorpha, Yarrowia lipolytica, Zygosaccharomyces bailii* and *Saccharomyces cerevisiae*.

8. The process of claim 1, comprising step (V), step (V) comprising one of the following reactions:
 (V-1) decarboxylating the aminobenzoic acid to give aniline;
 (V-2) decarboxylating the aminobenzoic acid to give aniline, followed by acid-catalyzed reaction of the aniline with formaldehyde to form di- and polyamines of the diphenylmethane series;
 (V-3) decarboxylating the aminobenzoic acid to give aniline, followed by acid-catalyzed reaction of the aniline with formaldehyde to form di- and polyamines of the diphenylmethane series, followed by reaction with phosgene to form di- and polyisocyanates of the diphenylmethane series;
 (V-4) decarboxylating the aminobenzoic acid to give aniline, followed by reaction of the aniline to give an azo compound;
 (V-5) reacting the aminobenzoic acid to give an amide; or
 (V-6) reacting the aminobenzoic acid to give conductive polymers.

9. The process of claim 8, comprising step (V-6), wherein the conductive polymer is polyanthranilic acid.

* * * * *